US011722486B2

(12) United States Patent
Outwater et al.

(10) Patent No.: US 11,722,486 B2
(45) Date of Patent: Aug. 8, 2023

(54) RANGE OF MOTION TRACKING SYSTEM

(71) Applicants: Chris Outwater, Santa Barbara, CA (US); William Gibbens Redmann, Glendale, CA (US)

(72) Inventors: Chris Outwater, Santa Barbara, CA (US); William Gibbens Redmann, Glendale, CA (US)

( * ) Notice: Subject to any disclaimer, the term of this patent is extended or adjusted under 35 U.S.C. 154(b) by 23 days.

(21) Appl. No.: 17/236,326

(22) Filed: Apr. 21, 2021

(65) Prior Publication Data
US 2021/0352066 A1 Nov. 11, 2021

Related U.S. Application Data

(63) Continuation of application No. 16/047,148, filed on Jul. 27, 2018, now abandoned, which is a continuation-in-part of application No. 15/284,157, filed on Oct. 3, 2016, now abandoned, which is a continuation of application No. 14/149,158, filed on Jan. 7, 2014, now Pat. No. 9,461,992.

(60) Provisional application No. 61/750,390, filed on Jan. 9, 2013, provisional application No. 62/537,777, filed on Jul. 27, 2017.

(51) Int. Cl.
| H04L 29/06 | (2006.01) |
| G06K 9/00 | (2022.01) |
| A61B 5/00 | (2006.01) |
| H04W 12/06 | (2021.01) |
| H04W 4/029 | (2018.01) |
| A61B 5/11 | (2006.01) |
| H04M 1/724 | (2021.01) |
| H04L 9/40 | (2022.01) |
| A61B 5/18 | (2006.01) |
| G06V 20/59 | (2022.01) |
| G06V 40/10 | (2022.01) |
| G06V 40/19 | (2022.01) |
| G06V 40/20 | (2022.01) |

(52) U.S. Cl.
CPC ........ *H04L 63/0861* (2013.01); *A61B 5/1114* (2013.01); *A61B 5/1121* (2013.01); *A61B 5/18* (2013.01); *A61B 5/4824* (2013.01); *A61B 5/6898* (2013.01); *G06V 20/597* (2022.01); *G06V 40/10* (2022.01); *G06V 40/19* (2022.01); *G06V 40/23* (2022.01); *H04L 63/083* (2013.01); *H04M 1/724* (2021.01); *H04W 4/029* (2018.02); *H04W 12/06* (2013.01); *A61B 5/1124* (2013.01); *A61B 2505/09* (2013.01); *H04L 63/0853* (2013.01); *H04M 2250/22* (2013.01)

(58) Field of Classification Search
CPC .. H04L 63/0861; H04L 63/083; H04W 4/029; H04W 12/06; H04M 1/724; G06V 40/10; G06V 20/597; A61B 5/6898

See application file for complete search history.

(56) References Cited

U.S. PATENT DOCUMENTS

| 4,857,916 A | 8/1989 | Bellin | G06K 9/00375 340/5.52 |
| 5,229,764 A | 7/1993 | Matchett | G07C 9/00158 340/5.52 |
| 7,562,218 B2 * | 7/2009 | Kirkup | G06F 21/35 713/168 |
| 8,051,468 B2 | 11/2011 | Davis | G06F 21/32 713/186 |
| 8,109,858 B2 | 2/2012 | Redmann | |
| 8,549,318 B2 | 10/2013 | White | |
| 2002/0174347 A1 * | 11/2002 | Ting | G06F 21/57 713/186 |
| 2004/0002894 A1 | 1/2004 | Kocher | G07C 9/00087 705/13 |
| 2004/0059923 A1 | 3/2004 | ShamRao | G06F 21/32 713/186 |
| 2006/0136741 A1 | 6/2006 | Mercredi | G06F 21/32 713/185 |
| 2006/0280340 A1 | 12/2006 | Derakhshani | G06K 9/00597 382/117 |
| 2007/0248242 A1 | 10/2007 | Ritter | G07C 9/00158 382/100 |
| 2008/0104415 A1 | 5/2008 | Palti-Wasserman | G06F 21/32 713/186 |
| 2008/0148393 A1 | 6/2008 | Wendt | G06F 21/32 726/19 |

(Continued)

FOREIGN PATENT DOCUMENTS

WO    WO2017/061890    4/2017

OTHER PUBLICATIONS

PCT International search report and opinion for PCT/US15/10409, dated Apr. 13, 2015 (PCT from instant application).

*Primary Examiner* — Yonas A Bayou
(74) *Attorney, Agent, or Firm* — Clifford H. Kraft

(57) ABSTRACT

A method for range of motion (ROM) tracking, that determines with a ROM tracking system, an exercise identified by a caregiver to be performed by a subject by positioning a sensor of the ROM tracking system to allow the sensor to detect at least one movement by the subject during a performance of the exercise, and then detecting, through the sensor, at least one movement of the subject. The system further analyzes the movement by the subject to determine a range of motion of the at least one movement; recording through a user interface an indication by the subject of an experiential narrative; and finally, providing a report to the caregiver, where the report contains the results of at least one movement in conjunction with at least a portion of the experiential narrative.

2 Claims, 5 Drawing Sheets

(56) References Cited

U.S. PATENT DOCUMENTS

| | | | |
|---|---|---|---|
| 2008/0166028 A1 | 7/2008 | Turek | G06K 9/0002 382/124 |
| 2008/0297589 A1* | 12/2008 | Kurtz | H04N 7/15 348/E7.083 |
| 2009/0024050 A1 | 1/2009 | Jung | A61B 5/16 600/544 |
| 2009/0083850 A1 | 3/2009 | Fadell | G06F 21/316 726/19 |
| 2010/0022351 A1* | 1/2010 | Lanfermann | A63B 24/0006 482/1 |
| 2010/0088023 A1* | 4/2010 | Werner | G09B 5/02 455/566 |
| 2010/0246902 A1 | 9/2010 | Rowe | G06K 9/00033 382/115 |
| 2011/0157347 A1 | 6/2011 | Kalocsai | |
| 2011/0197270 A1 | 8/2011 | Kaufman | G06F 21/32 726/7 |
| 2012/0022958 A1 | 1/2012 | de Sylva | G06Q 20/209 705/24 |
| 2012/0078473 A1 | 3/2012 | Ridder | A61B 5/0071 701/45 |
| 2012/0083668 A1 | 4/2012 | Pradeep | |
| 2012/0164978 A1 | 6/2012 | Conti | G06F 21/32 455/411 |
| 2013/0067551 A1* | 3/2013 | Frew | G06Q 20/40 726/7 |
| 2013/0133055 A1* | 5/2013 | Ali | H04W 12/065 726/7 |
| 2013/0141607 A1* | 6/2013 | Anabuki | H04N 23/62 348/222.1 |
| 2013/0171601 A1* | 7/2013 | Yuasa | G06V 40/23 434/258 |
| 2014/0154650 A1* | 6/2014 | Stack | A61B 5/4848 434/236 |

\* cited by examiner

RANGE OF MOTION TRACKING SYSTEM

This application claims priority from application Ser. No. 16/047,148 filed Jul. 27, 2018 which was a Continuation-In-Part of application Ser. No. 15/284,157 now abandoned which was a Continuation of application Ser. No. 14/149,158 now U.S. Pat. No. 9,461,992 issued Oct. 4, 2016 which claimed priority from U.S. Provisional Patent application 61/750,390 filed Jan. 9, 2013. Application 16/047,148 also claimed priority to U.S. Provsional Patent Application number 62/537,777 filed Jul. 27, 2017. Application Ser. Nos. 16/047,148, 15/284,157, 14/149,158 and 61/750,390 and 62/537,777 are hereby incorporated by reference in their entireties.

BACKGROUND

Field of the Invention

The present invention relates to systems that allows a caregiver to monitor a patient and more particularly to a range of motion tracking system.

Description of the Problem Solved

In the care of the elderly, it is difficult to accurately access a person's condition. It would be very advantageous to have an automated system that could accurately access and record a person's condition and range of motion.

Definitions

A "subject" is any person using the application of the present invention. A subject could be a patient, a customer, or client who is seeking an exercise program.

A "caregiver" is any person in authority who is enlisted by the subject to create, manage and control an exercise program. A caregiver could be a doctor, or nurse, or physical therapist, a trainer or a coach.

SUMMARY OF THE INVENTION

Embodiments of the present invention include a method for range of motion (ROM) tracking, that determines with a ROM tracking system, an exercise identified by a caregiver to be performed by a subject by positioning a sensor of the ROM tracking system to allow the sensor to detect at least one movement by the subject during a performance of the exercise, and then detecting, through the sensor, at least one movement of the subject. The system further analyzes the movement by the subject to determine a range of motion of the at least one movement; recording through a user interface an indication by the subject of an experiential narrative; and finally, providing a report to the caregiver, where the report contains the results of at least one movement in conjunction with at least a portion of the experiential narrative.

FIGURES

The following figures are from U.S. Pat. No. 9,461,992 incorporated by reference in its entirety.

DESCRIPTION OF THE PREFERRED EMBODIMENTS

Figure 1:
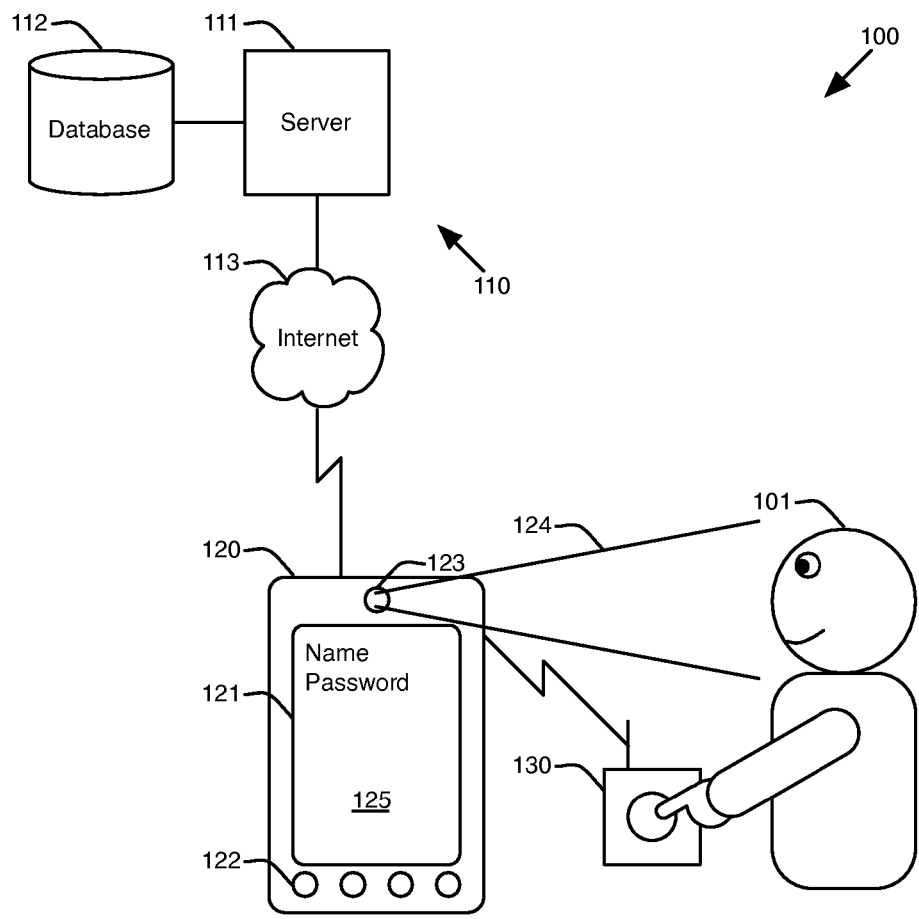
FIG. 1 shows a smartphone-based secure health testing and access system being used in one example of a self-enrollment process.

A range of motion tracking system is described. In one example embodiment, the range of motion tracking system is implemented with an application running on a smartphone. However, an actual smartphone is not strictly required, as would be apparent to one skilled in the art: In the alternative, a device comprising sufficient communication and processing capabilities able to execute methods for conveying instructions for an exercise to the user (e.g., by display or audio output), detecting and analyzing a subject's movements in the context of the exercise, and recording indication of pain level of the subject in conjunction with recording the range of motion, and communicating those records of range of motion and pain level to the caregiver.

The invention provides an evaluation system that engages subjects, e.g., the elderly and those requiring physical therapy, and encourages them to make specific movements or a series of movements, with the movements being measured by motion sensors. Said sensors will either be internal to the smartphone or external sensors in wired and/or wireless communication with the smartphone. The present invention builds a 3D "range of motion" map for specific portions of the subject's body, e.g., for movement of limbs where their joints that are under evaluation for various reasons, including surgery, trauma, old age, etc. The phone, or a sensor in communication with the phone, is held or else attached to a measurement zone, allowing the sensor to measure motions of the target portion of the subject's body, e.g., the target limb. The amount of pain during movement is also recorded based on indication by the subject, whether by voice or other user interface such as typing a value or description, or by control on a touchscreen or other graphic user interface to accept the pain level entry from the subject, or through a caregiver.

The invention is not limited to the injured and elderly and can be used by healthy, younger persons in order to track specific movements, or series of movements, for example ones that are suggested by a trainer or coach.

Further, a goal of the present improvement is to create both an educational and an evaluation system that can be easily employed and used by a single person at home without the aid of another person. Note that a subject might be alone at the time of exercise and evaluation.

In some embodiments, the system instructs and guides the subject through specific movements or exercises, and, at the same time uses the microphone internal to the smartphone, to record the subject's voice, use a voice recognition tool to recognize the subject's words, thereby "listening" to and record the subject as the subject describes the level of pain felt in conjunction with the measured movement.

The aim of most exercise therapy is to regain, or at least maintain, a range of motion that is perceived to be normal for the subject, for example, that which existed prior to an accident or surgery.

It is a goal of the present invention to improve the results of the training and therapy by combining a 3D range of motion map with the subject's verbal monologue, describing the level of pain, but not limited to pain, at any given point along the path of movement of the target limb. This is termed an "experiential narrative" and can include various sensations such as tingling, numbness, weakness, cold, warmth, tremors, etc.

If more than one portion of the body is to be evaluated (e.g., different limbs), the subject may describe to the audio input, or indicate using another user interface (e.g., typing or entry with a touchscreen control), which portions are being exercised or which exercise or motion is to be or has been performed. For some movements, the expected motions may produce measurements that are automatically recognizable, whereby providing a description from the subject is not needed. For an example of such technology, see U.S. Pat. No. 8,109,858. Similarly, if the particular body portion is identified, or the specific motion is prescribed by the invention, then it is not necessary for the subject to indicate the particular exercise.

The exercises or motions undertaken by the subject may be in compliance with instructions from the caregiver. Such instructions may be dispensed by the present invention, e.g., a smartphone application that announces the next exercise to be undertaken, which may include the instructions for how the subject is to hold the smartphone or how to attach the smartphone to the subject's body. The detection and recording of movement of the limb through space and the recording on the smartphone of the words, description and experiential narrative provided by the subject, are date and timestamped. The key concept is to build a connection in time between the subject's experience, which includes pain, and the 3D spatial map of movement of the limb. In one instance, this will be the subject's running monologue describing a level of pain based on common physical pain assessment descriptions from 1 to 10, ten being the most painful.

The spatial map is shown in one summary diagram, either animated or still, of the subject's movement with a color scheme from red to blue, with red as the highest pain level. Also, a series of summary diagrams are shown to the caregiver showing the subject's progress over time. This allows the caregiver to quickly and easily assess the subject's status.

Another attribute that will be described beside pain is "strength". The subject might not have pain, but might lose strength at a certain point along the path of movement, or perhaps the joint makes a concerning sound at a certain point and that sound will also be recorded for later analysis. This may all be described, keeping in mind that the level of pain during movement is the primary focus for most elderly and injured subjects.

The subject's voice will be recorded and time stamped so that the subject's words regarding pain, or other attributes as mentioned above, can be correlated with the subject's own movements; however, the voice recognition process does not need to be in real time, and may be processed locally or remotely (e.g., "in the cloud") at some reasonable time during, or after, the evaluation period. Remote voice recognition processing allows the application to take up less memory and processor power, compared with that processing taking place on the smartphone.

Another important attribute of the present invention is that the caregiver can review a session, once captured, to monitor the subject's recorded movements, range of motion, the number of repetitions, and the speed of each movement, as part of the prescribed exercise program. In some embodiments, during review, the system will record a caregiver comment in conjunction with the particular exercise or session being reviewed, for example to make recommendations, as needed, about the subject's exercise performance or progress.

The range of motion tracking system of the present invention performs the following steps:

Authenticating the identity of the subject. Authentication can be by account and password, but is preferably biometrically based, for example an image of the user's face, taken by a camera of the system, where the image is recorded in conjunction with the exercise, or is submitted for facial recognition to determine whether the image of the user's face is recognized as being the subject. If the authentication or any other data being recorded is categorized as patient data to be afforded privacy protections, then standard HIPAA precautions of encrypting sensitive data and confidentiality shall be followed.

Positioning at least a sensor of the system on the subject. At least a sensor of the system is held by or attached to the subject, in accordance with an instruction for an exercise. For example, the subject may attach the whole smartphone onto a particular (target) limb at a prescribed location. In some cases, multiple limbs can be tested and exercised at the same time, which may or may not require additional sensors; however, in general, a single limb, or a single joint, will be targeted, and the exercise and evaluation will be for just the one body portion.

A flexible band with velcro fastening, or other mounting, can be used to attach the sensor or smartphone to a limb. Instruction for attaching the sensor or smartphone to the limb or body portion indicates a consistent positioning and orientation on the limb or body portion. Consistency will provide the best results over a series of sessions. In the preferred embodiment a small motion sensor, rather than a phone, will be inserted into or contained in the band that is attached to the limb. Preferably, the velcro fastening allows the band to be to be secured in position, or released, with only one hand.

Providing instructions for an exercise to the subject. The subject will listen to directions from the smartphone in order to initiate an exercise and evaluation session and carry the session to its close. Instructions standardized for specific injuries and/or specific joints and limbs, may be selected by the caregiver, or customized instructions may be provided by the caregiver. For example, instructions for a shoulder, or knee, or hip, will be similar, but all different. In some embodiments, a video can be provided to the subject. In some embodiments, a record is made that the subject has seen the video, and may further record a signature of the subject to that effect. The instructions may be taken from a standard checklist of instructions for each limb.

A sample script:

"Extend your arm and let it rest at your side. As you slowly raise your arm from waist level to shoulder height, tell us if you have any pain. If yes, at what point does the pain begin? Using a range of 1 to 10, describe the pain as you move through the prescribed motion." In addition to the quantity of pain, there can also be descriptors for the quality of pain, such as dull, shooting or sharp, constant or only at a certain limit of movement. These qualifiers will all be noted as part of the subject's statement during the course of the session.

This detailed information will be part of the subject's education during the course of therapy, overlapping personal session data with data from a larger population of the same age and gender with the same or similar movement issues and with similar root causes, such as trauma, arthritis, etc. The technology will provide prognosis based on type of joint problem, age, gender, rehabilitation progress as sensed and recorded during recent sessions. In future embodiments, a dialogue will take place in which the smartphone becomes a virtual personal trainer/robot. The sessions will become a source of personalized learning and tracking progress. We must assume that the subject is in therapy because he or she values the full range of movement of their limbs and will be motivated to listen, to learn and to follow instructions.

Sessions will be tied in through and managed by systems such as Alexa. In another embodiment, this system will be used by a healthy person who wants to be certain that he or she is performing their exercises correctly. The movement information and data captured by the system will be sent to a the caregiver for evaluation.

In another embodiment in which an external sensor is used to track the motion of the limb(s), the smartphone's camera will be positioned to "watch" the subject using a pattern recognition technique and will combine this added optical information to the 3D map database and the subject's spoken words in order to give a more complete picture of the subject and the session. For an example of such technology, see VivoVR marketed by 3DiVi Inc., and described in international patent publication WO2017061890.

On the caregiver's, coach and physical therapist's side:

The caregiver advises his/her subject to download the application to their phone or tablet. They advise how to register and gain secure access to the application and the data that is kept with the application. Alternatively, a pre-loaded phone and sensor will be loaned to the subject.

In another embodiment, the caregiver, perhaps a nurse or doctor, can choose from a series of options for their patient(s), based on which joint(s) are under evaluation and/or therapy. Of course, all instructions and patient data will also be made available to a physical therapist chosen by the doctor.

A phone app or a browser on a computer connected to the Internet can be utilized for registering the subject into the database.

The patient can be confirmed and registered into the caregiver's system. After the subject is registered, he or she can follow instructions from the mobile device in order to set the baseline for the movement, reps, speed of movement, and range of motion of the target limb(s).

As described above, the 3D mapping data of the limb's movement and the subject's voice, or a written text of the subject's words, are correlated in time and a detailed report on range of motion and perceived pain is displayed as a 3D map for the caregiver on a device that is connected to the caregiver's system.

In one embodiment, the subject's avatar appears to move the target limb through a prescribed movement path as indicated by the caregiver. This will help the caregiver understand the path and the pain points along the path. In another embodiment, the inventors envision large data and predictive algorithms helping to coach the subject based on the real time measurements of range of motion and the pain description and historical data about similar subjects and similar injuries. Again, this technology will also pertain to healthy individuals who are trying to maintain or improve their strength and balance and endurance.

During a session, it is important that the subject carefully stretches the envelope of movement, but does not go too far. In this manner, an interactive program can be created in which the program itself monitors the range of motion and the perceived pain level, monitoring and instructing the subject regarding repetitions and range of motion.

A history of these reports is created in order to determine changes, a patient's improvement or degradation, or lack of cooperation can be noted in the file. Using the envisioned technology and system the caregiver will gain improved data about their subjects that will help improve the overall process, and help the caregiver or trainer make the most informed treatment and exercise decisions optimized for their subjects.

The following is the text of U.S. Pat. No. 9,461,992 incorporated by reference into this application in its entirety.

Smartphone Based Identification, Access Control, Testing, and Evaluation

Field

The present invention relates to the field of identification, access control and evaluation and more particularly relates to using a smartphone in this application.

DESCRIPTION OF THE PRIOR ART

The modern mobile communication device, such as the cellular telephone or so-called smart cellular telephone (smartphone) has become almost ubiquitous in society. Most adults and teenagers routinely carry these devices as well as a number of younger children. The smartphone incorporates considerable processing power and sophisticated communications with a powerful display system and embedded sensors.

The smartphone also promises to become the portal allowing secure personal authentication, mental and physical evaluation and secure access control. The smartphone will become the preferred tool for the "accountable care process", and everything that this proposed health insurance system contemplates will demand both secure identification and ubiquitous ease of use for quickly and repeatedly determining levels of health and competence over a wide range of activities, as well as subsequent calculation of the risks within a group of insured individuals.

Risk management will become the primary focus of health providers as they navigate the new health insurance frontiers. They must inform and motivate their partners and customers so that they can mitigate their risks. Patients will strive to be healthier because they will be rewarded for their efforts. Health teams will be organized and promoted. Effective, inexpensive tools for monitoring health will be in great demand.

Biometric ID hardware and software will be readily available on many smartphones. Fingerprint, facial recognition, voice recognition will all be used to secure the ID and to access information. This will be especially true for individuals who are seeking help in maintaining their health at specific levels. Employers will be instilling a "team spirit" as all employees strive to maintain the costs of health care for their group.

SUMMARY

The present invention presents a suite of testing and evaluation tools that run in conjunction with a smartphone that can be used to both enroll individuals and subsequently allow such enrollees to gain secure access so that the program may measure, track and report on tests, including activities, that may indicate general health and wellness status. Here, the word "smartphone" includes any handheld or mobile device containing at least one processor. The smartphone can be used as the platform for this suite of tools that can include applications that run independently on the smartphone device or in communication with it, but can also include sensors and other data acquisition tools that can be peripheral to the smartphone and connected by wire or wirelessly.

As a first step in the process, the present invention utilizes biometric and PIN techniques to enroll and identify patients. Next, the smartphone can be used to both identify enrollees and to directly monitor external conditions. The present invention comprises a suite of access, testing and evaluation tools, whether running local applications (apps), communicating with remote, cloud based servers, or a combination of these to attain a secure and efficient testing platform that can be used by enrollees to measure, track and report on tests, including activities that may indicate health and wellness status. The smartphone is used as the platform for this suite of tools that can include applications that run independently on the smartphone device, but can also include sensors and other data acquisition tools that can be peripheral to the smartphone and connected by wire or wirelessly. Such basic health parameters as temperature, pulse, blood oxygen, blood pressure, weight, and the like can also be captured by the mobile device. The present invention uses the existing data capture and display and kinetic measurement devices inherent to the modern mobile communication devices, such as smartphones, to utilize the enrollee's visual, auditory and tactile senses in order to determine general physical and mental health status and alertness. These may all be used n order to calculate a general wellness status and derive a risk profile. In another embodiment the present invention can determine and control access to vehicular assets.

EMBODIMENTS

FIG. 1 shows one of the first steps in the process of the present invention: enrollment. Enrollment 125 (on screen 121) depends on the proper identity of the enrollee 101; therefore, various levels of identity assurance can be used to authenticate and confirm an enrollee's identity. As mentioned, many smartphones 120 are progressing to biometric based access to the wireless phone's basic operations. During online or in-person enrollment, the enrollee 101 can create a secure account by taking a smartphone photo 124 with camera 123 of a certified picture ID (not shown) such as a passport, drivers license, or both. It is well known in the art that hardware and software already exists for photographically scanning checks and credit cards. Similar software can be used to scan certified photos to complement existing personal identity verification tools. This graphical information can be tied to the smartphone telephone number and can be checked against the identity of the registered owner of the telephone. This information can also be tied to any other biometrics that are required for access to the phone's operation. The required number and nature of biometrics, whether facial recognition (using photo 124 of enrollee), voiceprint, spoken passphrase (microphone not shown), fingerprint 130, etc., depends on the policy of the administrative entity and the level of security required.

FIG. 1 shows a self-enrollment process with the system of the present invention. For any heightened access level a (live) photo 124 of the enrollee can be submitted and a voice pattern (not shown) or fingerprint, using sensor 130, can be given. This might be required for doctors and nurses to write to and modify an existing enrollee record based on HIPPA regulations. Any latency in voice and/or image data recording and transmission can be accounted for, and the data can be correlated and processed on high speed servers 111 in a cloud server environment (i.e., through Internet 113) or elsewhere. All data can be tied to the enrollee's personal account 112. The enrollee can allow various levels of access to the personal account based on HIPPA rules, policy, as may health coaches, insurance companies, nurses, law enforcement, and the like.

Figure 2:
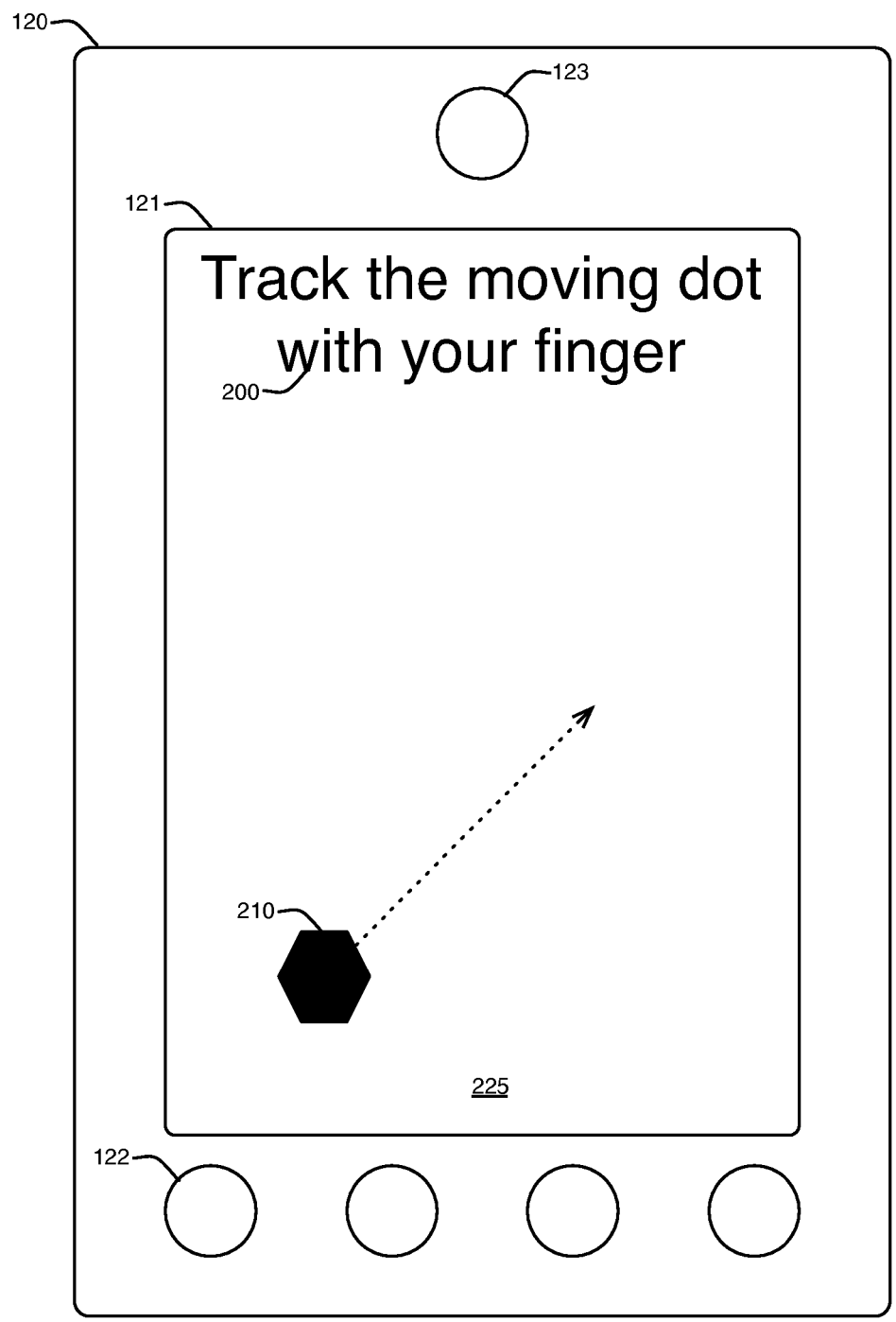
FIG. 2 shows the use of a smartphone-based secure health testing and access system in use for one example kinetic assessment.

FIG. 2 shows, in a particular embodiment of the present invention, kinetic testing in conjunction with voice or visual instructions 200. Instructions to move, transfer from one hand to another, screen 121 face up, screen 121 face down, graphical arrow on screen up, arrow on screen down. Actions such as keeping an arrow always facing up by rotating the phone as the arrow rotates on screen is also possible. Other instructions based on color are also possible, such as, if arrow turns from red to blue, point the arrow down. This type of testing is a valuable tool in accessing the general neurological condition of the subject. It can thus be used for general assessment by first responders and, outside the medical realm by police. Another example test, shown in FIG. 2, direct the subject to track the moving dot 210 on screen 121 with their finger (if screen 121 is a touchscreen), or with controls, e.g. 122, otherwise.

This process can also be used as an assessment and access tool for vehicles of all types. The smartphone can be wirelessly tuned to an on-board device (OBD) and could be tied to mandatory access testing for at risk individuals with some record of criminal activity such as a parolee or a person previously convicted of driving under the influence of alcohol or drugs. Access can range from small motor vehicles to major vehicular assets such as planes, ships, trains, and the like. Owners and enforcement officials can choose from a suite of smartphone-based tests based on enrollee's profile and a range of security and risk management demands.

Figure 3A:
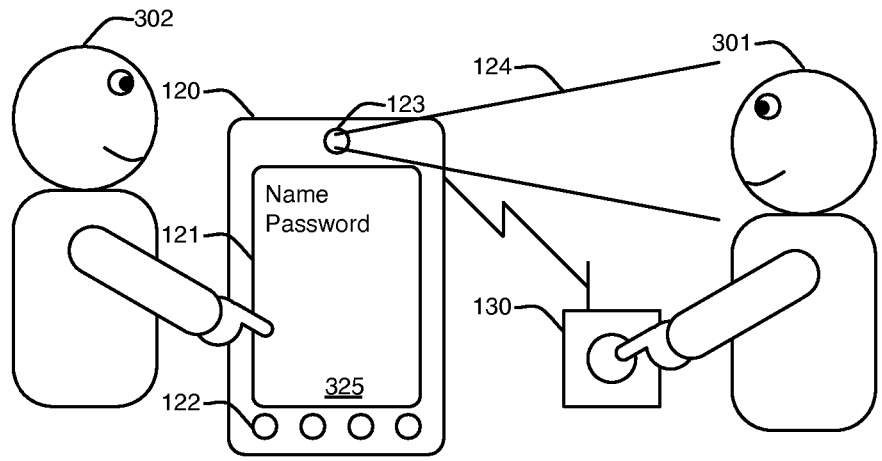
FIG. 3A shows a smartphone-based secure health testing and access system being used in one example secure enrollment process monitored by an authorized third person.
Figure 3B:
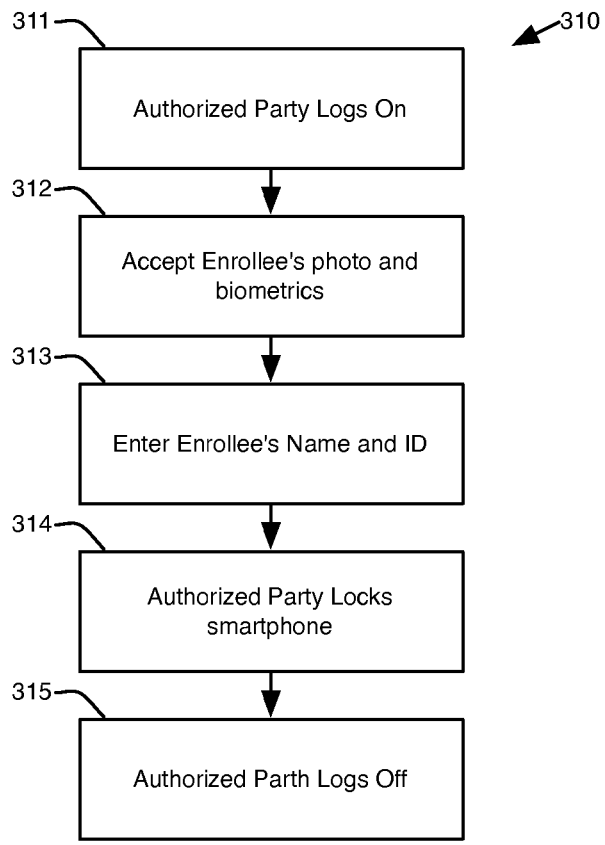
FIG. 3B is a flowchart for that monitored enrollment process.

FIG. 3A illustrates and enrollment procedure 325 for use in some higher security applications, there may be need for a person of authority 302 to register the owner 301 of the smartphone using a secure password or other means of identification. The smartphone is the key or portal to virtual or real world access to people, places and objects of value, such as, machines, vehicles, devices, locations, and other access. In some cases the enrollee 301 is enrolled not by himself (as enrollee 101 was in FIG. 1), but by a person of authority 302 who locks-in the enrollee's ID into the smartphone and a chosen list of functions by virtue of a secure password or biometric such that the attachment of the smartphone to that enrollee cannot be changed without knowledge of the password and the biometrics of the enroller 302. This secure administrative process can take place in person or in an online registration session. FIG. 3B shows the secure registration process 310 for a third person beginning at step 311 where the authorized party 302 logs on. At step 312, the enrollee's 301 photo 124 and biometrics (e.g., fingerprint via reader 130) are accepted. At step 313, the enrollee's name and ID are entered, e.g. via form 325 on screen 121 or photo of ID as described above. At step 314 the authorized party 302, having at least monitored the performance of steps 312, 313, locks-in the enrollee's ID into the smartphone, and subsequently (in step 315) logs off.

The present invention provides a suite of access, testing and evaluation tools whether running local applications (apps) on smartphone 120, or apps communicating with remote, cloud-based 113 servers III (or local servers), or a combination of these to attain a secure and efficient testing platform that can be used by enrollees 101, 401 to measure, track and report on tests, including activities (e.g., as shown in FIG. 2) that may indicate the health and wellness status. The smartphone 120 can be used as the platform for this suite of tools that can include applications that run independently on the smartphone device, but can also include sensors and other data acquisition tools (e.g., fingerprint sensor 130) that can be peripheral to the smartphone and connected by wire or wirelessly. Such basic health parameters as temperature, pulse, blood oxygen, blood pressure, weight, and the like can thus be captured by the mobile device. The present invention can use the existing data capture, display and kinetic measurement devices inherent to the modern mobile communication devices, such as smartphones, to utilize the enrollee's visual, auditory and tactile senses in order to determine general physical and mental health status and alertness which may all be used in order to calculate a general wellness status and derive a risk profile, not only a health risk profile, but in another embodiment discussed below in conjunction with FIGS. 4A and 4B, to determine and control access to vehicular assets. Ease of use and frequency of use is vital, thus the ubiquitous mobile device, with all of its built-in data capture and display devices, or a similar device is important to the invention.

In a particular embodiment, the camera, microphone and LCD screen, accelerometers and vibration device can be used to test the alertness of the enrollee. This can be done by testing various senses: visual, auditory, tactile in conjunction with measuring the reaction time to each requested operation by the enrollee. This process and the instructions should be language neutral, that is, either in the language of the enrollee's preference, or in a pictographical (i.e., non-text) form.

For example, it is well known in the art of neurological evaluation that eye movement and tracking is indicative of alertness and neurological well-being. The smartphone can be used as a tool to track eye movement and reaction time in response to certain stimuli. Typically, in the reverse camera mode shown in FIG. 4A, the enrollee's 401 image 124 of himself (and whatever background is present) fills the screen 425. With a custom app, the viewing screen presentation 425 can be divided showing a smaller image of the enrollee and his eyes (not shown), while another part of the screen can be used to show a variety of graphic images in various locations on the screen or moving across the screen (similar to screen presentation 225 in FIG. 2). The enrollee would have a contour on the screen to show the recommended distance of the phone from his face. Facial recognition can be used not only for ID, but also to make certain that the face is the proper orientation and distance from the reverse camera during the eye tracking evaluation.

The objects to be tracked can be as simple as a dot or a circle (see hexagon 210, FIG. 2). Images can also be flashed on the screen for various periods of time. Words and/or letters can be presented, and the enrollee can be asked to read the word or touch some image on the phone's LCD screen that relates to the word. This can be based on native language, but can also be language independent. Short term memory can also be tested by showing an image of an object, a letter, a number and asking the enrollee to indicate what he saw, and the sequence of what he saw by saying the name or number, or pressing a location on the LCD screen.

The most appropriate eye tracking system for evaluation, training or access will depend on the type of eye movements (i.e., fixations, saccades, and pursuits) that comprise the complex eye movements used for visual skills (e.g., spotting, localization, scanning, tracing, tracking) which are being evaluated/trained or tested for visually guided activities of daily living (e.g., reading, face recognition and television watching) or for access.

A history and data record of previous biometric sign-on and access control and test performance can be further used to build a profile that can be used to provide identification of the enrollee before, during and after the evaluation. A performance that is out of the curve for some reason can raise doubts on the authentication and identification process and result in a demand further access controls which may include third party verification (as in FIG. 3), or additional or repeated tests.

A simple test example is an application that shows a dot on the screen and instructs the enrollee to follow the dot's movement on the screen. This can be done by eye alone, or the enrollee could be asked to also follow with his finger. The size, shape and speed of dot can vary with the range of difficulty. Vibration can be tied to the testing such that the phone vibrates as long as the finger is on or near the moving dot, or vice versa. The movement of the dot is known, and the movement of the finger(s) can be registered from touch sensors on the screen. Alternatively, instructions can be given that if the phone vibrates, move the phone in some spatial pattern. This can also be used to test pain and range of motion in elderly patients, especially those who might have trouble coming in for examinations. The requested movement could be accompanied by verbal and visual and tactile clues. Vibration is an important clue in that it should be in contact with the enrollee and can enhance kinetic cues in addition to images and sounds.

Balance and direction can also be tested by moving the smartphone through space at the proper orientation based on graphic or verbal instructions sent to the enrollee. This can further evaluate the ability of the enrollee to perform certain tasks.

In all such tests, the tests and test scores can be remembered for comparison and also for assessment and allowing access to a vehicle or other access. Nuanced enrollee ID can be based on tilt, angle, key touch location and timing. This can be combined with running tests to enhance enrollee ID.

The profile of the enrollee can include personal ID and at least one other attribute such as age and gender. Other attributes can be added as desired. A profile can be constructed that creates a benchmark for certain activities and reaction times compared to people with the same or similar characteristics in the larger population.

Figure 4A:
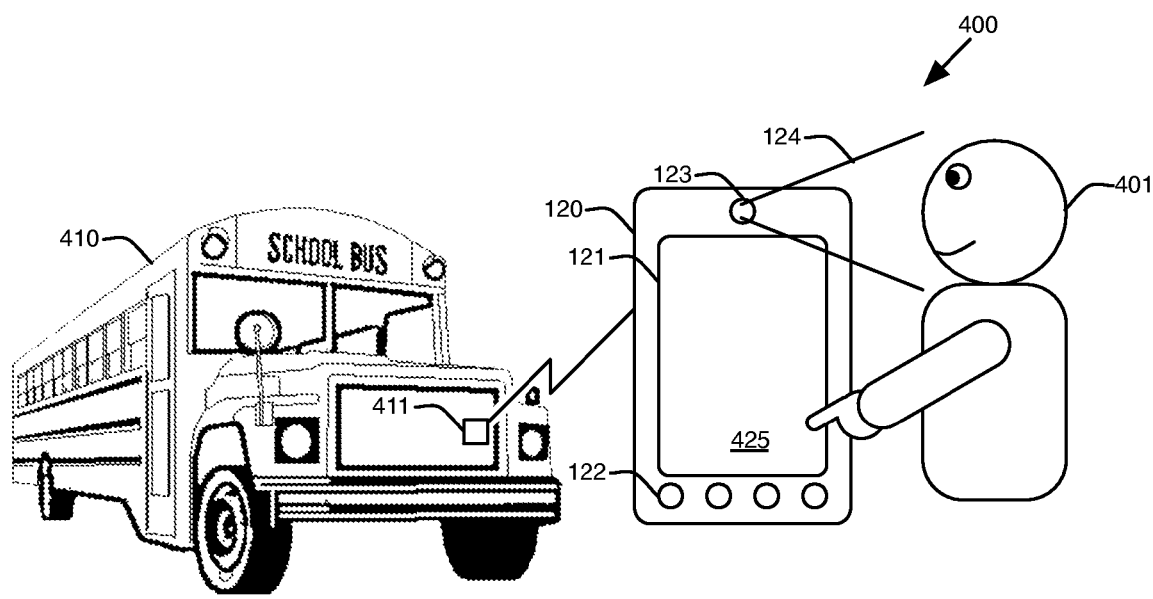
FIG. 4A shows a smartphone-based secure health testing and access system connected to the OBD connector of a vehicle for access control.
Figure 4B:
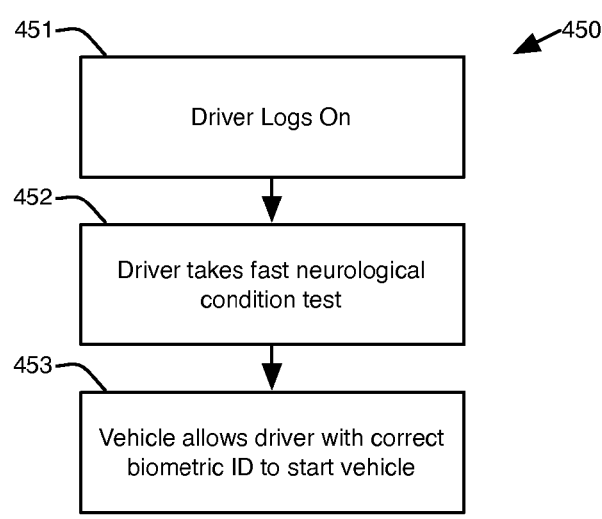
FIG. 4B is a flowchart for that secure access process.

FIG. 4A illustrates another embodiment of the invention, where the alertness testing application on the smartphone 120 can be tied by wire or wirelessly to a vehicle 410 or machine access control device. This may not be only for access, but also for authenticated transactions coming through the vehicle's dashboard application. This may also be tied to vehicle identification such as a license plate. Access to drive can also be tied to access to goods and services in a specific location based on the smartphone and its communication link with the vehicle, the identity of the vehicle and the identity of the driver as determined via the driver's smartphone, which can be running one of the applications previously described.

In a modern vehicle 410, a smartphone application can be tied to the OBD (onboard diagnostic) connector 411 standardized by the Society of Automobile Engineers (SAE), or other, which may be provided with a wired or wireless interface, that allows certain individuals to access a vehicle based on photos and perhaps a phrase and/or voiceprint sent from the smartphone to a remote control center and an access code sent to the phone via cellular modem, and then from the phone 120 to the vehicle 410 via OBD 411. This is very efficient in that the command itself can be matched with an authenticated voiceprint.

For example, in some instances access would be allowed based only on photo-based identification, while other access could be authenticated via face and voice, depending on policy. Such applications can also be tied to general access and the phone's GPS, user ID (UID, i.e., username) and password could be used in addition to facial and voice recognition. The back-facing camera image of the enrollee's face would have to be consistent with stored images and consistent during the testing and evaluation. A series of images, numbers, words can be shown to the enrollee. This could also be as simple as asking the enrollee to hold the main screen up to a mirror while he sees specific letters (mirror corrected in the application) and other images for his recognition and verbal confirmation. If not performed properly within a set period of time, the test is failed, and access to a vehicular asset (e.g., 410) could be denied. This is summarized by the testing and access process 450 shown in FIG. 4B, which begins at step 451 when the enrollee 401 (the driver) logs on to the smartphone 120 application. At step 452, the driver takes a brief test, e.g., to test his current neurological condition. Upon verifying the test was passed, at step 453, the smartphone 120 communicates via the OBD connection 411 and allow the driver, having demonstrated a valid identification and neurological state, to start the vehicle. The above test could also be used for medical and health assessment.

In some embodiments of the invention, enrollees are welcome to work together and share tests in health groups or independently. Health-based social networking is possible and encouraged. Activities and milestones such as pulse, blood oxygen, blood pressure, and alertness may all be used to form a general wellness status.

Figure 5:
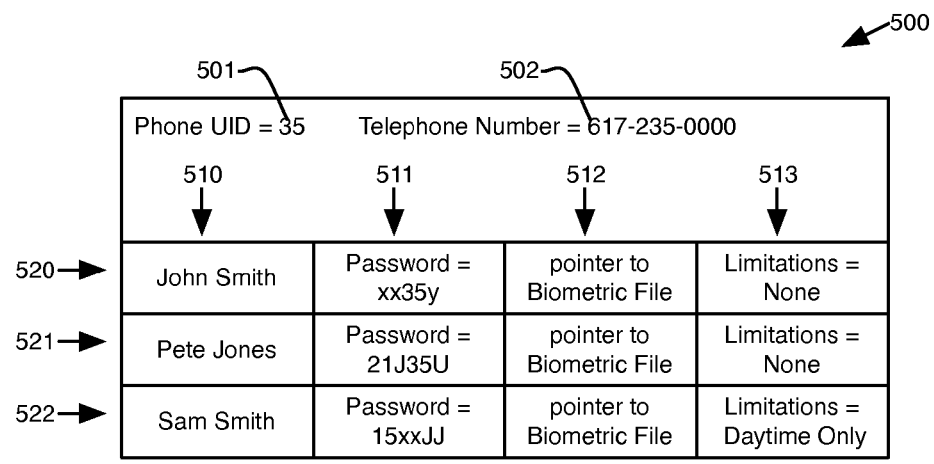
FIG. 5 shows a database record representative of multiple enrollees associated with a single mobile device.

In the preferred embodiment, one person is typically registered and tied to one mobile device; however, in other embodiments, such as shown in FIG. 5, multiple persons 510 can securely register and sign on (e.g., with the corresponding password 511 and biometric information 512, to a single, shared mobile device 501 and telephone number 502, or several devices (not shown), and the authenticated input from a plurality of secure devices can be collated and shared from a remote, secure database 112. Certain individuals 520, 521 may have no particular limitation 513, but other individuals (e.g., 522) may have access that is further limited (e.g., only allowed access during the daytime).

The present invention provides a unique way of using a smartphone to test, evaluate and control access that will prove cheap to implement and efficient to use.

Several descriptions and illustrations have been provided that aid in understanding the present invention. One with skill in the art will realize that numerous changes and variations can be made without departing from the spirit of the invention. Each of these changes and variations is within the scope of the present invention.

A suite of testing and evaluation tools that run in conjunction with a smartphone that can be used to both enroll, and for subsequent enrollees, to gain secure access so that the program may measure, track and report on tests, including activities, that may indicate general health and wellness status. Here, the word "smartphone" includes any handheld or mobile device containing at least one processor. The smartphone can be used as the platform for this suite of tools that can include applications that run independently on the smartphone device, but can also include sensors and other data acquisition tools that can be peripheral to the smartphone and connected by wire or wirelessly.

The invention claimed is:

1. A method for range of motion (ROM) tracking comprising:
   providing to a subject, with a ROM tracking system, an exercise identified by a caregiver to be performed by the subject;
   positioning a sensor of the ROM tracking system to allow the sensor to detect a set of movements by the subject during a performance of the exercise;
   detecting, by the ROM tracking system, through the sensor, the set of movements performed by the subject during the performance of the exercise;
   after completion of the exercise by the subject, providing a 3-dimensional range of motion map of the set of movements performed by the subject during the performance of the exercise;
   creating with the ROM tracking system an educational tool and an evaluation system easily employed and used by a single person at home without aid of another person.

2. The method of claim 1 further comprising recording, by the ROM tracking system through a first user interface (UI) of the ROM tracking system, a description of pain felt by the subject during the performance of the exercise.

* * * * *